(12) United States Patent
Kim et al.

(10) Patent No.: US 8,465,962 B2
(45) Date of Patent: Jun. 18, 2013

(54) MICROORGANISM HAVING ENHANCED L-VALINE PRODUCTIVITY AND METHOD FOR PRODUCING L-VALINE USING THE SAME

(75) Inventors: Hye Won Kim, Gyeonggi-do (KR); Ji-Hye Lee, Gyeonggi-do (KR); Soo Youn Hwang, Gyeonggi-do (KR); Jong Hyun Kim, Busan (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/310,536

(22) Filed: Dec. 2, 2011

(65) Prior Publication Data

US 2013/0045511 A1    Feb. 21, 2013

(30) Foreign Application Priority Data

Aug. 16, 2011    (KR) .................. 10-2011-0081146

(51) Int. Cl.
*C12N 1/20* (2006.01)
*C12N 15/00* (2006.01)
*C12P 13/08* (2006.01)

(52) U.S. Cl.
USPC .................. 435/252.32; 435/320.1; 435/115

(58) Field of Classification Search
None
See application file for complete search history.

(56) References Cited

U.S. PATENT DOCUMENTS

| 3,893,888 A | 7/1975 | Tsuchida et al. |
| 3,970,519 A | 7/1976 | Tsuchida et al. |
| 5,521,074 A | 5/1996 | Katsumata et al. |
| 7,632,663 B1 | 12/2009 | Eggeling et al. |

FOREIGN PATENT DOCUMENTS

| EP | 0 287 123 A2 | 10/1988 |
| EP | 1346027 B1 | 9/2003 |
| JP | 63-160592 A | 7/1988 |
| KR | 90-007948 B1 | 10/1990 |
| KR | 1995-0005133 B1 | 5/1995 |
| KR | 1996-0016871 B1 | 12/1996 |
| KR | 2002-0057470 A | 7/2002 |
| KR | 10-2006-0039992 A | 5/2006 |

OTHER PUBLICATIONS

Ambe-Ono et al., "Improved L-Leucine Production by an α-Aminobutyric Acid Resistant Mutant of *Brevibacterium lactofermentum*," Biosci. Biotech. Biochem. 60(8):1386-1387, 1996.
Kisumi et al., "Isoleucine Accumulation by Regulatory Mutants of *Serratia marcescens*: Lack of Both Feedback Inhibition and Repression," Journal of Bacteriology 110(2):761-763, 1972.
Radmacher et al., "Linking Central Metabolism with Increased Pathway Flux: I-Valine Accumulation by *Corynebacterium glutamicum*," Applied and Environmental Microbiology 68(5):2246-2250, 2002.
Tsuchida et al., "Production of L-Valine by 2-Thiazolealanine Resistant Mutants Derived from Glutamic Acid Producing Bacteria," Agr. Biol. Chem. 39(6):1319-1322, 1975.
Elišáková et al., "Feedback-Resistant Acetohydroxy Acid Synthase Increases Valine Production in *Corynebacterium glutamicum*," Applied and Environmental Microbiology 71(1):207-213, Jan. 2005.
Krause et al., "Increased Glucose Utilization in *Corynebacterium glutamicum* by Use of Maltose, and Its Application for the Improvement of L-Valine Productivity," Applied and Environmental Microbiology 76(1):370-374, Jan. 2010.

*Primary Examiner* — Yong Pak
(74) *Attorney, Agent, or Firm* — SEED IP Law Group PLLC

(57) ABSTRACT

The present invention relates to a microorganism having an enhanced L-valine productivity and a method for producing L-valine using the same. More particularly, the present invention relates to a *Corynebacterium glutamicum* mutant strain that has resistance to L-valine and derivatives thereof so as to have an enhanced L-valine productivity, and a method for producing L-valine using the same.

4 Claims, 1 Drawing Sheet

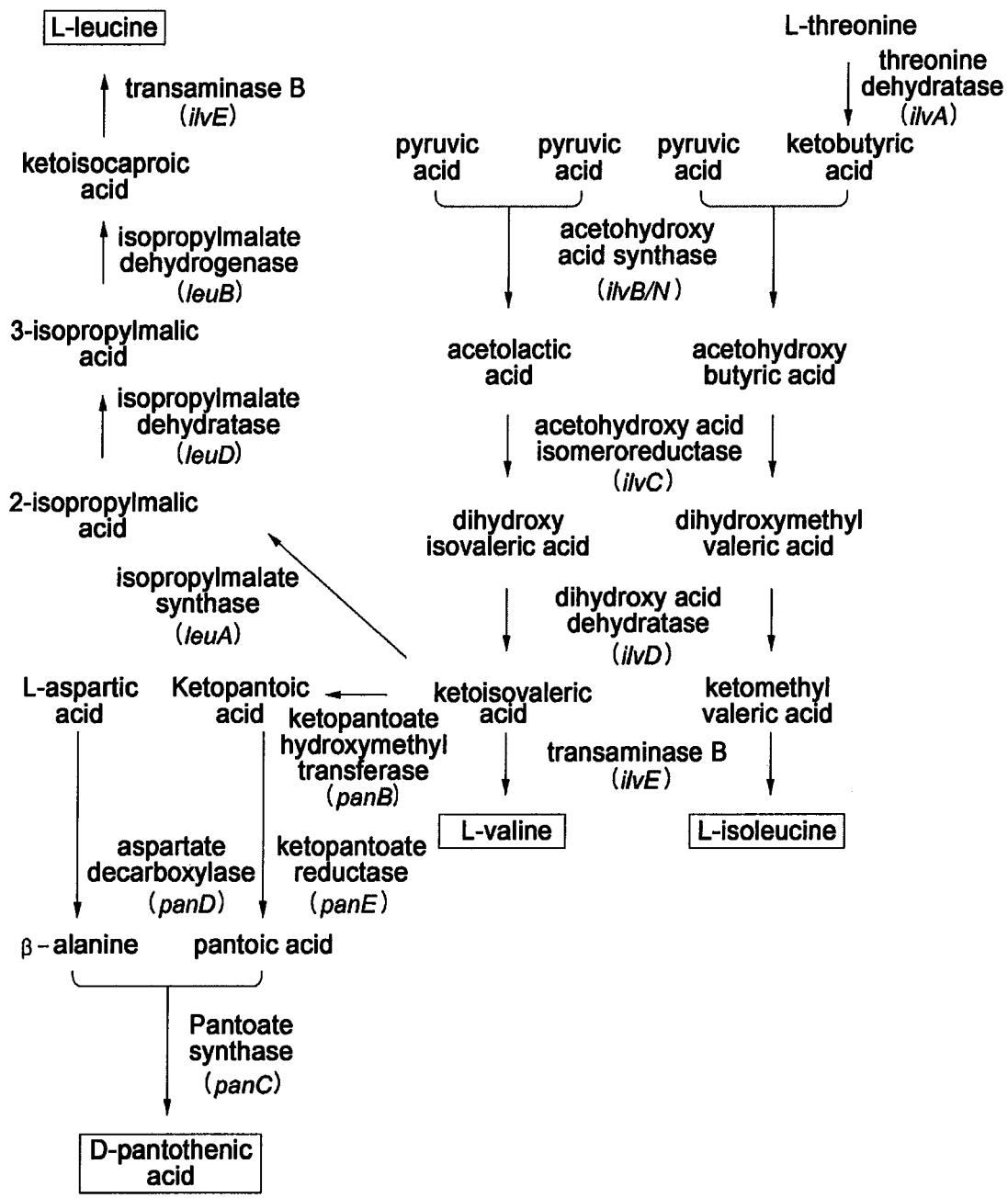

MICROORGANISM HAVING ENHANCED L-VALINE PRODUCTIVITY AND METHOD FOR PRODUCING L-VALINE USING THE SAME

BACKGROUND OF THE INVENTION

1. Field of the Invention

The present invention relates to a microorganism having an enhanced L-valine productivity and a method for producing L-valine using the same.

2. Description of the Related Art

L-amino acids are used in human medicine, in particular, in the pharmaceutical industry, food industry and animal nutrition or the like. Particularly, branched-chain amino acids refer to three amino acids among nine essential amino acids: L-valine, L-leucine, and L-isoleucine. Unlike other amino acids, which are mostly metabolized in the liver, branched-chain amino acids are mainly metabolized in the muscle tissue and serve as an energy source during exercise. As branched-chain amino acids are known to play an important role in muscle maintenance and growth during exercise, their use is growing. Specifically, L-valine has been used as a feed component, because it was reported that L-valine has high reducing power and serves to improve lactational performance of sows. L-valine has also been used in infusion solutions and amino acid complexes for medical purposes, and in health supplements and beverage additives.

A microorganism used for the production of L-amino acids is represented by coryneform bacteria, particularly *Corynebacterium glutamicum*. Due to the high importance of coryneform bacteria in industrial production, methods for producing L-amino acids using the microorganisms are continuously undergoing improvement. For example, improvements are being made to improve the method relating to stirring and introducing oxygen, or compositions of the culture media such as sugar concentration during fermentation. To improve the L-amino acid productivity of these microorganisms, selection and mutant selection methods are widely employed. For example, there is a method of selecting and using microorganisms that are resistant to antimetabolites such as an isoleucine derivative, isoleucine hydroxamate (Kisumi M et al., (1972) Journal of Bacteriology 110: 761-763), an L-valine derivative, 2-thiazole alanine (Tsuchida T et al., (1975) Agricultural and Biological Chemistry, Japan 39: 1319-1322) or a leucine derivative, α-aminobutyrate (Ambe-Ono Y et al., (1996) Bioscience Biotechnology Biochemistry 60: 1386-1387), or auxotrophic for metabolites having regulatory relevance and produce L-amino acids (Eva Radmacher et al., (2002) Applied and Environmental Microbiology, Vol. 68 p. 2246-2250).

Meanwhile, one of the branched-chain amino acids, L-valine is biosynthesized in a microorganism, starting from pyruvic acid via acetolactic acid, dihydroxy isovaleric acid, and ketoisovaleric acid. These intermediate metabolites are produced by catalytic activities of acetohydroxy acid synthase, acetohydroxy acid isomeroreductase, dihydroxy acid dehydratase, and transaminase B. However, these enzymes are also involved in L-isoleucine biosynthesis starting from ketobutyric acid and pyruvic acid, and L-leucine is also biosynthesized from the intermediate metabolite, ketoisovaleric acid via 2-isopropylmalic acid, 3-isopropylmalic acid, and ketoisocaproic acid. Therefore, since the enzymes used in the biosynthetic pathways of the branched-chain amino acids, namely, L-valine, L-isoleucine, and L-leucine are identical, it is difficult to produce only one of the branched-chain amino acids by industrial fermentation. Additionally, feedback inhibition by the final product L-valine or derivatives thereof occurs, which makes it difficult for industrial mass production of L-valine.

To solve these problems, many studies have been made to develop L-valine-producing microorganisms having resistance to L-valine or derivatives thereof for the production of L-valine, and they are exemplified by a method of using a microorganism having resistance to D, L-amninobutyric acid (Japanese Patent Laid-Open No. 563-160592), a method of using a microorganism that is resistant to thiazole alanine and auxotrophic for leucine, isoleucine, or threonine (Japanese Patent Laid-Open No. 552-116), a method of using a microorganism having resistance to amnioethylcysteine (Japanese Patent Laid-Open No. S58-2678), a method of using a microorganism having resistance to L-valine in an acetic acid-supplemented medium and having sensitivity to pyruvic acid in a glucose-supplemented medium (U.S. Pat. No. 5,521,074, Korean Patent No. 1995-0005133), a method of using a microorganism having resistance to polyketide (Korean Patent No. 1996-0016871) or the like.

However, currently developed L-valine-producing microorganisms are resistant only to a single material or a limited material of L-valine or derivatives thereof, and thus there is still a need to develop L-valine-producing microorganisms having a resistance to various materials involved in the feedback control of L-valine biosynthesis.

For these reasons, the present inventors have made many efforts to develop microorganisms capable of producing L-valine in a higher yield than other conventional strains. As a result, they found that a mutant strain, obtained from a glutamic acid-producing microorganism, produces L-valine in a high yield, and has resistance to numerous L-isoleucine derivatives and L-valine derivatives, specifically, α-aminobutyric acid (ABA), α-hydroxyvaline (AHV), thiazole alanine (TA), and norvaline (NV), thereby completing the present invention.

SUMMARY OF THE INVENTION

An object of the present invention is to provide an L-valine-producing *Corynebacterium glutamicum* mutant strain KCCM11201P.

Another object of the present invention is to provide a method for producing L-valine using the mutant strain.

BRIEF DESCRIPTION OF THE DRAWINGS

FIG. 1 shows a biosynthetic pathway of L-valine as the final product of the present invention.

DETAILED DESCRIPTION OF THE PREFERRED EMBODIMENTS

In one embodiment, the present invention provides an L-valine-producing *Corynebacterium glutamicum* mutant strain KCCM11201P.

As used herein, the term "L-valine" means an L-amino acid having a chemical formula of $(CH_3)_2CHCH(NH_2)COOH$, which is one of the essential amino acids and structurally belongs to the branched-chain amino acids, together with L-leucine and L-isoleucine.

Meanwhile, L-valine biosynthesis in a microorganism is as shown in FIG. 1, in which L-valine is biosynthesized starting from pyruvic acid via acetolactic acid, dihydroxy isovaleric acid, and ketoisovaleric acid. In addition, the biosynthetic pathway is catalyzed by enzymes such as acetohydroxy acid synthase, acetohydroxy acid isomeroreductase, dihydroxy acid dehydratase, and transaminase B. However, these enzymes are identically used in the biosynthetic pathways of the branched-chain amino acids, namely, L-valine, L-isoleucine, and L-leucine, and thus it is difficult to produce only one of the branched-chain amino acids by industrial fermentation. In particular, feedback inhibition by the final product L-valine or derivatives thereof occurs, which makes it difficult to perform industrial mass production of L-valine. By solving the problem, the mutant strain of the present invention is a novel microorganism that has resistance to L-valine or derivatives thereof so as to remove the feedback inhibition, thereby showing enhanced L-valine productivity.

Preferably, the mutant strain of the present invention may have resistance to valine or derivatives thereof, isoleucine or derivatives thereof.

As used herein, the term "derivative" means the known compounds that induce the feedback inhibition regarding biosynthesis of the final product L-valine so as to reduce production of L-valine in the microorganism, and an example of L-isoleucine derivatives can be α-aminobutyric acid and L-valine derivatives, alpha-hydroxyvaline, thiazole alanine, and norvaline or the like, but is not limited thereto. Preferably, the mutant strain may have resistance to one or more substances selected from the group consisting of valine, α-aminobutyric acid, alpha-hydroxyvaline, thiazole alanine, and norvaline. Most preferably, it may have a resistance to all of the valine, α-aminobutyric acid, alpha-hydroxyvaline, thiazole alanine, and norvaline.

Generally, it is known that L-valine biosynthesis is inhibited when L-valine is accumulated to a certain level in a cell. Therefore, the strain having resistance to the derivatives releases the inhibition from L-valine and thus can produce even at a high concentration. According to one embodiment of the present invention, the present inventors employed a method of selecting microorganisms capable of producing a high level of L-valine by using the derivatives. Further, since L-isoleucine is an amino acid that is produced by a biosynthetic pathway identical to the L-valine biosynthetic pathway, the strains capable of producing a high level of L-valine can be also selected by analyzing whether the strains acquire resistance to the isoleucine derivatives. Thus, the isoleucine derivatives are also used to select the strains capable of producing a high level of L-valine.

According to the present invention, a mutant strain having an enhanced L-valine productivity is selected from the parental strains by mutation. In this regard, the mutations in the microorganism can be induced by a variety of techniques widely known in the art, and any one of physical and chemical mutagenic factors may be used. Examples of the chemical mutagenic factor suitable for the present invention include N-Methyl-N'-nitro-N-nitrosoguanidine (NTG), diepoxybutane, ethyl methane sulfonate, mustard compounds, hydrazine, and nitrous acid, but are not limited thereto. In addition, Examples of the physical mutagenic factor may include ultraviolet and gamma radiation, but are not limited thereto.

Upon the induction of mutations, the parental strain is affected by a mutagenic factor at an intensity sufficient to leave a particular size of surviving populations. The size varies depending on the type of mutagenic factors, and depends on the amount of mutations induced in the surviving populations at a given killing rate. For example, the desired killing rate for NTG should leave approximately 10%-50% of the starting population. Nitrous acid mutagenesis should leave approximately 0.01% to 0.1% of the starting population and ultraviolet mutagenesis should leave approximately 1.0%. According to an embodiment of the present invention, NTG is used to induce mutations in the parental strain, in order to prepare a mutant strain having an enhanced L-valine productivity.

In one Example of the present invention, an L-glutamic acid-producing *Corynebacterium glutamicum* KFCC 10661 (Korean Patent Application No. 1988-0016543; Publication No. 1990-0007948) was used as a parental strain, in order to prepare the mutant strain having an enhanced L-valine productivity, which is attributed to the property of requiring 1 molecule of glutamic acid during the L-valine biosynthesis.

Therefore, random mutagenesis was performed in the glutamic acid-producing *Corynebacterium glutamicum* KFCC 10661 as a parental strain, and the microorganism was spread on a minimal medium supplemented with the isoleucine derivative, α-aminobutyric acid (ABA) and the valine derivatives, alpha-hydroxyvaline (AHV), thiazole alanine (TA) and norvaline (NV). Subsequently, a mutant strain having a common resistance to the derivatives at each concentration of 20 mM, 20 mM, 40 mM and 50 mM was selected, and designated as *Corynebacterium glutamicum* CA08-0072. Further, it was confirmed that L-valine production of the mutant strain having a common resistance was increased to 4 times or higher than that of the parental strain (see Table 1). The *Corynebacterium glutamicum* mutant strain CA08-0072 was deposited in the international depository authority, Korean Culture Center of Microorganisms, which is located at 361-221, Hongje-1-dong, Seodaemon-gu, Seoul, Korea, on Jul. 13, 2011, and assigned accession number KCCM11201P.

In another embodiment, the present invention provides a method for producing L-valine, including the step of culturing the mutant strain in a culture medium.

Preferably, the method for producing L-valine may further include the step of recovering L-valine from the culture medium of the mutant strain.

As used herein, the term "culturing" means to grow a microorganism under artificially controlled conditions. In the present invention, the method for culturing the *Corynebacterium glutamicum* CA08-0072 mutant strain (KCCM11201P) for the production of L-valine may be conducted using a culturing method of *Corynebacterium glutamicum* widely known in the art. Specifically, examples of the culturing method include batch culture, continuous culture, and fed-batch culture, but are not limited thereto. These various methods are disclosed in, for example, "Biochemical Engineering" (James M. Lee, Prentice-Hall International Editions, pp 138-176, 1991) or the like.

The medium used for the culture has to meet the requirements for the culture of a specific strain. The culture media for *Corynebacterium* strain are described (e.g., Manual of Methods for General Bacteriology. American Society for Bacteriology. Washington D.C., USA, 1981). Possible carbon sources may include sugars and carbohydrates such as glucose, saccharose, lactose, fructose, maltose, starch, and cellulose, oils and fats such as soy bean oil, sunflower oil, peanut oil, and coconut fat, fatty acids such as palmitic acid, stearic acid, and linolic acid, alcohols such as glycerol and ethanol, and organic acids such as acetic acid. These substances may be used individually or as mixtures. Possible nitrogen sources may include peptone, yeast extract, meat extract, malt extract, corn steep liquor, soy bean flour and urea, or inorganic compounds such as ammonium sulfate, ammonium chloride, ammonium phosphate, ammonium carbonate and ammonium nitrate. The nitrogen sources may be used individually or as mixtures. Possible phosphorus sources may include potassium dihydrogen phosphate or dipotassium hydrogen phosphate or the corresponding sodium-containing salts. Furthermore, the culture medium has to include metal salts such as magnesium sulfate and ferric sulfate that are necessary for growth. In addition to the above substances, essential growth substances, such as amino acids and vitamins, may be included. Appropriate precursors may be also added to the culture media. The above-mentioned substances may be suitably added to the culture medium in batch culture or in continuous culture during cultivation.

pH of the culture may be adjusted by suitably adding basic compounds such as sodium hydroxide, potassium hydroxide, and ammonia, or acidic compounds such as phosphoric acid and sulfuric acid. The generation of air bubbles may be inhibited by using an antifoaming agent such as fatty acid polyglycol ester. To maintain aerobic condition, oxygen or oxygen-containing gas (e.g., air) may be injected into the culture. Generally, the temperature of the culture medium is 20 to 45° C. The cultivation may be continued until the production of L-valine reaches a desired level. This objective is normally achieved within 10 to 160 hours. L-valine may be released into the culture medium or included within the cells.

The method for producing L-valine of the present invention includes the step of recovering L-valine from the cells or culture medium. The method for recovering L-valine from the cells or culture medium may be performed by a conventional method known in the art, for example, centrifugation, filtration, anion exchange chromatography, crystallization, and HPLC, but is not limited thereto. According to an embodiment of the present invention, a supernatant, obtained by centrifuging the culture medium at a low speed and removing biomass, is separated by ion exchange chromatography.

Hereinafter, the present invention will be described in detail with reference to the following Examples. However, these Examples are for illustrative purposes only, and the invention is not intended to be limited by these Examples.

EXAMPLE 1

Selection of Mutant Strain by Artificial Mutagenesis

To obtain mutant strains having an enhanced L-valine productivity, mutation of a microorganism was induced using the following method.

Specifically, a parental strain, glutamic acid-producing *Corynebacterium glutamicum* KFCC-10661 (Korean Patent Publication No. 1990-0007948), which had been previously activated by cultivation on an activation medium for 16 hours, was cultivated for 14 hours on a seed medium that was sterilized at 121° C. for 15 minutes. Then, 5 mL of the culture medium was collected and washed with 100 mM citrate buffer. NTG (N-Methyl-N'-nitro-N-nitrosoguanidine) was added thereto at a final concentration of 200 mg/L. After 20 minutes, the medium was washed with 100 mM phosphate buffer. The strains treated with NTG were spread on a minimal medium and the death rate was measured. As a result, the death rate was 85%.

In order to obtain mutant strains having a common resistance to α-aminobutyric acid (ABA), alpha-hydroxyvaline (AHV), thiazole alanine (TA) and norvaline (NV), the NTG-treated strains were spread on a minimal medium containing ABA, AHV, TA and NV at a final concentration of 20 mM, 20 mM, mM and 50 mM, respectively. Then, the strains were cultivated at 30° C. for 5 days to obtain a mutant strain having a common resistance to ABA, AHV, TA and NV.

The obtained mutant strain was designated as *Corynebacterium glutamicum* CA08-0072, and was deposited in the Korean Culture Center of Microorganisms on Jul. 13, 2011, and assigned accession number KCCM11201P.

The media used in Examples 1 and 2 have the following compositions.

<Activation Medium>
Beef extract 1%, Polypeptone 1%, Sodium Chloride 0.5%, Yeast Extract 1%, Agar 2%, pH 7.2

<Seed Medium>
Glucose 5%, Bacto Peptone 1%, Sodium Chloride 0.25%, Yeast Extract 1%, Urea 0.4%, pH 7.2

<Minimal Medium>
Glucose 1.0%, Ammonium Sulfate 0.4%, Magnesium Sulfate 0.04%, Potassium Dihydrogen Phosphate 0.1%, Urea 0.1%, Thiamine 0.001%, Biotin 200 µg/L, Agar 2%, pH 7.0

EXAMPLE 2

Examination of L-Valine Productivity of L-Valine-Producing Mutant Strain

The *Corynebacterium glutamicum* CA08-0072 (KCCM11201P) having a common resistance to high concentrations of ABA, AHV, TA, and NV, which was obtained in Example 1, was cultured by the following method, in order to examine its L-valine productivity.

The parental strain *Corynebacterium glutamicum* KFCC 10661 and the mutant strain were inoculated into 250 ml-corner baffle flasks containing 25 ml of the seed medium and cultured at 30° C. for 20 hours with shaking at 200 rpm to obtain seed culture media. Thereafter, 1 ml of each of the seed culture media was inoculated into a 250 ml-corner baffle flask containing 24 ml of the following production medium, and cultured at 30° C. for 72 hours with shaking at 200 rpm to produce L-valine.

The production medium used in the present Example 2 has the following composition.

<Production Medium>
Glucose 5%, Ammonium Sulfate 2%, Potassium Dihydrogen Phosphate 0.1%, Magnesium Sulfate Heptahydrate 0.05%, CSL (corn steep liquor) 2.0%, Biotin 200 µg/L, pH 7.2

After the completion of cultivation, high speed liquid chromatography was performed to determine the amounts of the produced L-valine. The concentrations of L-valine in the culture media of the experimental strains are summarized in Table 1, below.

TABLE 1

Comparison of L-valine productivity of *Corynebacterium glutamicum* CA08-0072 (KCCM11201P)

| | *Corynebacterium glutamicum* KFCC 10661 (Parental strain) | *Corynebacterium glutamicum* CA08-0072 (Mutant strain) |
|---|---|---|
| L-valine concentration (g/L) | 0.5 | 2.1 |

As shown in Table 1, the parental strain, *Corynebacterium glutamicum* KFCC 10661 produced 0.5 g/L of L-valine, but the mutant strain *Corynebacterium glutamicum* CA08-0072 according to the present invention produced 2.1 g/L of L-valine, indicating that its L-valine productivity is about 4 times or higher than that of the parental strain.

The above result suggested that the mutant strain having a resistance to L-valine, L-isoleucine and derivatives thereof is not affected by feedback inhibition, thereby producing L-valine in high efficiency and high yield.

Effect of the Invention

The coryneform microorganism of the present invention has a resistance to L-valine, L-isoleucine and derivatives thereof, and thus is not affected by feedback inhibition of L-valine so as to have enhanced L-valine productivity. Therefore, the method for producing L-valine using the microorganism of the present invention is used to produce L-valine in high efficiency and high yield.

What is claimed is:

1. An L-valine-producing *Corynebacterium glutamicum* mutant strain KCCM11201P.

2. The mutant strain KCCM11201P according to claim 1, wherein the mutant strain has resistance to α-aminobutyric acid (ABA), α-hydroxyvaline (AHV), thiazole alanine (TA) and norvaline (NV).

3. A method for producing L-valine, comprising culturing KCCM11201P of claim 1 in a culture medium to produce L-valine, and recovering L-valine from the culture medium.

4. The method according to claim 3, wherein the cultivation is performed at a temperature of 20 to 45° C. under aerobic condition for 10 to 160 hours.

* * * * *